United States Patent [19]

Beckh et al.

[11] Patent Number: 5,037,990
[45] Date of Patent: Aug. 6, 1991

[54] SULPHONAMIDES CONTAINING A TETRAZOLYL RADICAL

[75] Inventors: Hansjörg Beckh, Bürstadt; Ernst-Christian Witte, Mannheim; Karlheinz Stegmeier, Heppenheim; Leisel Doerge, Lampertheim, all of Fed. Rep. of Germany

[73] Assignee: Boehringer Mannheim GmbH, Mannheim, Fed. Rep. of Germany

[21] Appl. No.: 401,317

[22] Filed: Aug. 31, 1989

[30] Foreign Application Priority Data

Aug. 31, 1988 [DE] Fed. Rep. of Germany ....... 3829431

[51] Int. Cl.[5] .................. C07D 257/02; C07D 257/06
[52] U.S. Cl. ...................................... 548/251; 548/253
[58] Field of Search ........................ 548/253, 252, 251

[56] References Cited

FOREIGN PATENT DOCUMENTS

65505/86 11/1986 Australia .
0239907A1 10/1987 European Pat. Off. .

OTHER PUBLICATIONS

Buchanan et al, J. Med. Chem. 16, pp. 174 & 175 (1973).

Primary Examiner—David B. Springer
Attorney, Agent, or Firm—Armstrong, Nikaido, Marmelstein, Kubovcik & Murray

[57] ABSTRACT

The present invention provides sulphonamides of the general formula:

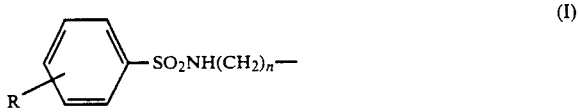

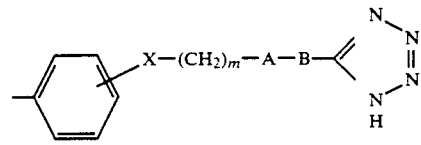

wherein R is a hydrogen or halogen arom, a cyano group or a $C_1$-$C_6$-alkyl or trifluoromethyl radical, n is 1, 2 or 3, m is 0 or 1 to 5, X is a valency bond, an oxygen atom, a carbonyl group or a —CHOH— group, A is a valency bond or a carbonyl group and B is a valency bond or an —NH— group; the physiologically acceptable salts thereof with inorganic and organic acids, as well as the optical isomers thereof.

The present invention also provides processes for the preparation of these compounds and pharmaceutical compositions containing them.

19 Claims, No Drawings

SULPHONAMIDES CONTAINING A TETRAZOLYL RADICAL

The present invention is concerned with new sulphonamides containing a tetrazolyl radical, processes for the preparation thereof and pharmaceutical compositions containing them.

The new sulphonamides according to the present invention are compounds of the general formula:

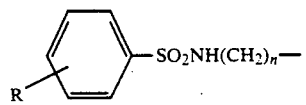
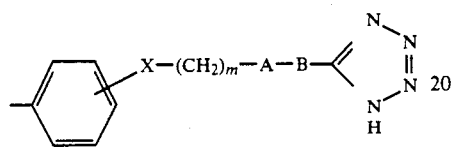
(I)

wherein R is a hydrogen or halogen atom, a cyano group or a $C_1$-$C_6$-alkyl or trifluoromethyl radical, n is 1, 2 or 3, m is 0 or 1 to 5, X is a valency bond, an oxygen atom, a carbonyl group or a —CHOH— group, A is a valency bond or a carbonyl group and B is a valency bond or an —NH— group, and the physiologically acceptable salts thereof with inorganic and organic bases.

When the compounds of general formula (I) contain an asymmetric carbon atom, the present invention also includes the optically-active compounds and racemic mixtures thereof.

The new compounds of general formula (I) display an outstanding antagonistic action towards thromboxane $A_2$, as well as against prostaglandin endoperoxides. They inhibit the aggregation of blood platelets and prevent the constriction of the smooth musculature, as well as bronchoconstriction. Furthermore, they are valuable medicaments for the treatment of pathological changes of the kidney function.

These properties make the new compounds according to the present invention valuable medicaments for the treatment of, for example, cardiovascular diseases and asthma and for the prophylaxis of the shock lung. In addition, they can be used in the case of organ transplants and kidney dialysis and are suitable for the prevention of recidivity in the case of gastric ulcers. An especial importance is the possibility of being able favourably to influence or to prevent thrombotic processes. They can be used for the treatment of peripheral arterial occlusive diseases and can be used, for example, against cerebral ischaemic states.

If R is an alkyl radical, then it can be straight-chained or branched. Preferred alkyl radicals R include methyl, ethyl, propyl, isopropyl, butyl, sec.-butyl, tert.-butyl, pentyl and hexyl radicals.

The halogen atoms are fluorine, chlorine or bromine atoms and preferably chlorine or bromine atoms.

The substitution in the righthand phenyl ring is preferably in the 3- or 4-position.

Compounds are preferred in which n is 2.

The new compounds according to the present invention can be prepared by one of the following processes:

a) reaction of a compound of the general formula:

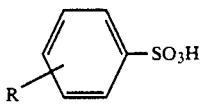
(II)

in which R has the same meaning as above, or a reactive derivative thereof with a compound of the general formula:

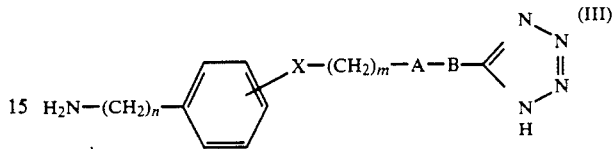
(III)

in which A, B, X, n and m have the same meanings as above; or b) reaction of a nitrile of the general formula:

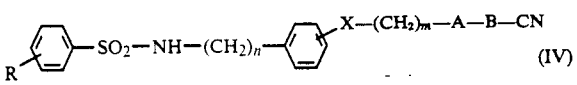
(IV)

in which R, A, B, X, n and m have the same meanings as above, with hydrazoic acid or a salt thereof; or c) when A is a —CO— group and B is an —NH— group, reaction of a carboxylic acid of the general formula:

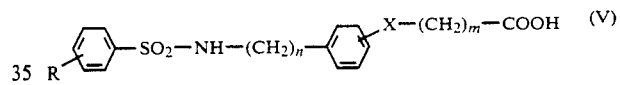
(V)

in which R, X, n and m have the same meanings as above, or a reactive derivative thereof, by which is to be understood an ester, for example a methyl, cyanomethyl, ethyl or p-nitrophenyl ester, an anhydride, an amide, for example an imidazolide, or an acid halide, for example an acid chloride or acid bromide, with 5-amino-1,2,3,4-tetrazole of the formula:

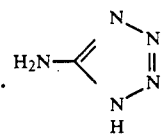
(VI)

which can also be used as the hydrate; or d) when a is a —CO— group, B is an —NH— group and m is 1, reaction of a substituted malonic acid of the general formula:

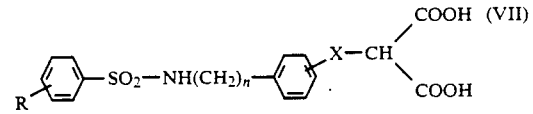
(VII)

in which R and n have the same meanings as above and X is an oxygen atom or a —CO— group, or a reactive derivative of one of the two carboxyl groups, with 5-amino-1,2,3,4-tetrazole, optionally in the form of the hydrate, and subsequent removal of the free carboxyl group under decarboxylation conditions; whereafter, if desired, a compound (I) thus obtained is subsequently converted into a different compound (I), and, if desired, the compound (I) obtained is converted into a physiologically acceptable salt by neutralisation with a non-toxic base.

The compounds of general formula (II) are known from the literature. Some of the compounds of general formula (III) are new. Thus, for example, compounds in which X is an oxygen atom, B is an —NH— group and A is a —CO— group can be obtained in known manner by reacting an aminoalkylphenol protected on the amino group with a halocarboxylic acid, followed by condensation of the carboxyl group with 5-aminotetrazole (VI).

They can also be obtained by condensation of an aminoalkylphenol, protected on the amino group, of the general formula:

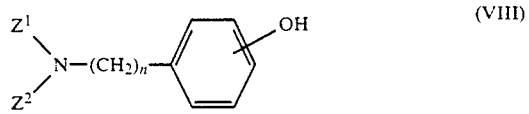

in which $Z^1Z^2N$— is, for example, a benzyloxycarbonylamino radical or a phthalimino radical or an acylamino, benzylamino or dibenzylamino radical but can also be an arylsulphonylacylamino or an arylsulphonylalkylamino radical, with a compound of the general formula:

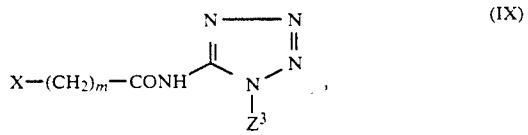

in which X is a reactive group and preferably a halogen atom or an alkyl (aryl)sulphonyl radical, m has the same meaning as above and $Z^3$ is a protective group and preferably a benzyl radical, and possibly subsequent removal of the protective groups $Z^1Z^2$, as well as $Z^3$.

Another method of preparation starts from hydroxybenzaldehydes: condensation of a hydroxybenzaldehyde with a halocarboxylic acid of the general formula:

X—(CH$_2$)$_m$—COOH    (X)

in which X and m have the same meanings as above, to give a compound of the general formula:

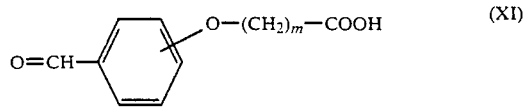

in which m has the same meaning as above, which is reacted with 1H-5-aminotetrazole to give a compound of the general formula:

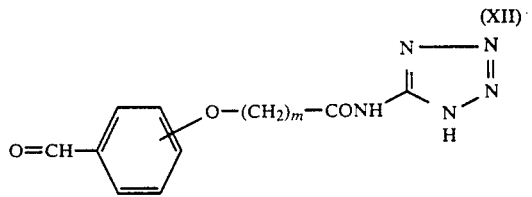

in which m has the same meaning as above.

Condensation of the compound (XII) with nitromethane and hydrogenation/reduction of the resulting nitrostyrene of the general formula:

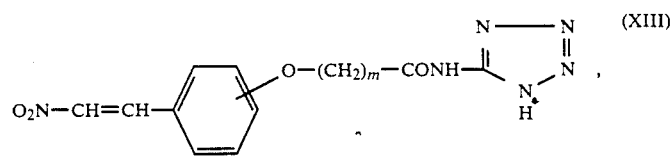

in which m has the same meaning as above, provides the desired compound (III).

Alternatively, a hydroxynitrostyrene of the general formula:

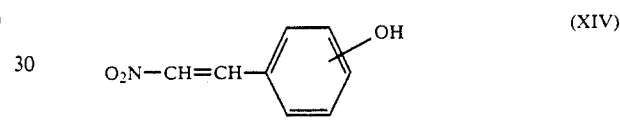

can first be reacted with a halocarboxylic acid (X), then with 1H-5-aminotetrazole, in which case compounds (XIII) are again obtained which have to be hydrogenated/reduced.

It is also possible to react a nitrostyrene (XIV) with a compound of the general formula (IX) and subsequently to hydrogenate/reduce the compound thereby obtained. If $Z^3$ is a benzyl radical, then this is thereby also removed.

The starting material for the preparation of compounds (III) can also be a hydroxybenzyl cyanide of the general formula:

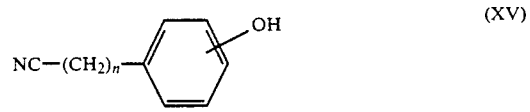

in which n has the same meaning as above.

Reaction with a halocarboxylic-acid (X) and thereafter with 1H-5-aminotetrazole gives a compound (XVI) ($R^3$=H), condensation of which with a compound (IX) gives a compound (XVI) which carries a protective group $Z^3$ on the nitrogen atom:

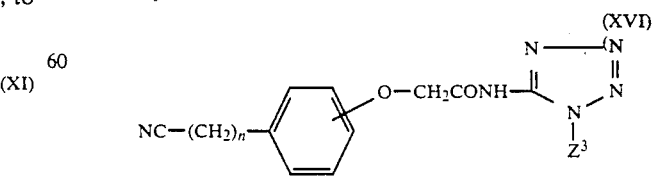

in which n and $Z^3$ have the same meanings as above, whereafter there follows a reduction of the nitrile group and possibly splitting off of the protective group $Z^3$.

The compounds of general formula (VII) are also new. When X is an oxygen atom, these compounds can be obtained by reacting a compound of the general formula:

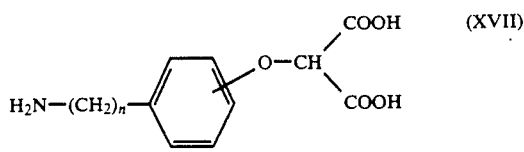

in which n has the same meaning as above, with a sulphonic acid of general formula (II).

The compounds (XVII) in which n is 2 can be obtained in several ways:

Condensation of a hydroxynitrostyrene (XIV) with chloromalonic acid ester in the presence of one equivalent of alkali gives a compound of the general formula:

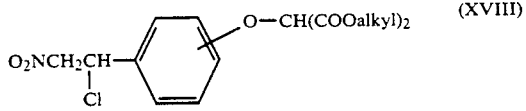

which is converted into the diester (XVII) by hydrogenation.

In the presence of two equivalents of alkali, there is obtained an O-substituted nitrostyrene of the general formula:

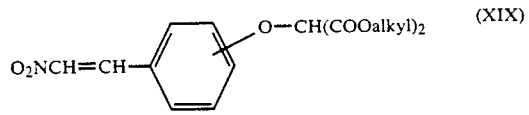

which can, of course, also be obtained by reacting a hydroxybenzaldehyde with a chloromalonic acid diester to give a compound of the general formula:

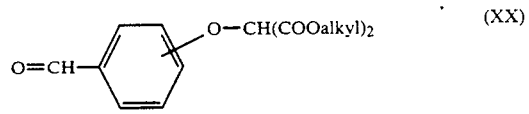

followed by condensation with nitromethane. The nitrostyrene (XIX) is subsequently hydrogenated/reduced.

Without limitation with regard to the value of n, as starting material for the preparation of compounds (XVII) there can be used an N-protected aminoalkylphenol of the general formula:

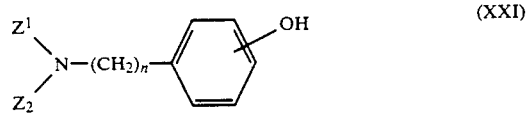

in which $Z^1$, $Z^2$ and n have the same meanings as above.

It is condensed with a halomalonic ester and subsequently freed from the protective group. Preferred protected amino groups $Z^1Z^2N$— here include the benzyloxycarbonylamino, benzylamino, dibenzylamino and acetylamino radicals.

In the case of compounds in which A is a valency bond, the corresponding nitriles are used as starting materials which are reacted with hydazoic acid to give the tetrazole.

When X is a valency bond, A is a —CO— group and B is an —NH— group, the starting materials are phenylalkylcarboxylic acids, which are known from the literature, which are again condensed with 5-aminotetrazole. When A is a valency bond and B is an —NH— group, corresponding N-cyanoaralkylamines of the general formula:

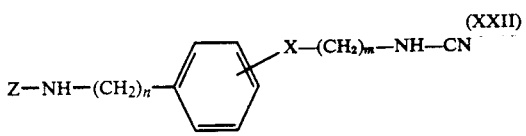

in which n, m and X have the same meanings as above and Z is a protective group, are reacted with hydrazoic acid to give the corresponding aminotetrazole derivatives. The N-cyanoamino compounds are obtained by reacting the corresponding amine with cyanogen bromide.

The reaction of a compound of general formula (II) with one of general formula (III) advantageously takes place in a solvent or solvent mixture, for example dichloromethane, diethyl ehter, tetrahydrofuran, dioxan or benzene, possibly in the presence of an acid-binding agent, for example sodium carbonate, triethylamine or pyridine, in which case the latter two can simultaneously also serve as solvent, in the presence of an agent activating the acid or removing water, for example thionyl chloride or phosphorus pentachloride, but preferably with a reactive derivative of a compound of general formula (II), for example an anhydride or halide thereof, preferably at a temperature of from 0° to 100° C., for example at a temperature between ambient temperature and 50° C.

The salts of hydrazoic acid which can be reacted in the process according to the present invention with the nitriles (IV) can be, for example, alkali metal salts, for example lithium azide, sodium azide or potassium azide, alkaline earth metal azides, for example magnesium azide, calcium azide or strontium azide, or metal salts, for example aluminium azide, tin azide, zinc azide or titanium azide, salts with organic bases, for example ammonium azide or aniline azide and the like. In some cases, it is advantageous not to use the pure azide but rather in admixture with, for example, ammonium chloride or with an alkylammonium chloride or also in combination with a Lewis acid, for example aluminium chloride, tin chloride, zinc chloride or titanium tetrachloride. In this case, the alkali metal salts of hydrazoic acid react with ammonium chloride, alkylammonium chloride or the Lewis acid to give the corresponding salt, for example ammonium azide, alkylammonium azide, aluminium azide, tin azide, zinc azide or titanium azide, which reacts with the nitrile (IV). The combination of the alkali metal azides with ammonium chloride, alkylammonium chloride or the Lewis acid gives especially good yields.

The hydrazoic acid or salts thereof, as well as the Lewis acid or ammonium chloride or alkylammonium chloride, which are used in combination with the alkali metal azides, are used in 1 to 10 molar excess, referred to the nitrile (IV).

The reaction is advantageously carried out in an organic solvent, for example a hydrocarbon, such as benzene, toluene or petroleum ether, in an ether, such as tetrahydrofuran, dioxan or diethyl ether, or in an aprotic polar solvent, such as dimethylformamide, dimethyl sulphoxide or 1-methyl-2-pyrrolidinone.

The reaction conditions, such as temperature, pressure and time, are not subject to any special limitations but the reaction is usually carried out at a temperature of from ambient temperature to 180° C., at a pressure of from normal pressure to 160 bar. and with a reaction time of from 30 minutes to 48 hours.

If a salt of hydrazoic acid is used, because of the acidity of the hydrogen atom of the tetrazolyl group, the product precipitates out as the corresponding salt and can be isolated as such. By treatment with a mineral acid, for example hydrochloric acid or sulphuric acid, there is obtained the compound of general formula (I) with a free tetrazolyl group.

The products can be isolated and purified in known manner, for example by fractionation corresponding to the dissociation of the hydrogen atom of the tetrazolyl group, by chromatography or by recrystallisation.

The preferred method for the reaction of the aminotetrazoles (VI) with the carboxylic acids of the general formula (V) consists in the reaction of about equimolar amounts of the amine and of the acid in the presence of an agent removing water. For this purpose, there can be used, for example, polyphosphoric acid which then serves simultaneously as solvent or isobutyl chloroformate in the presence of an aprotic polar solvent, for example dimethylformamide.

The reactions take place between 50° and 200° C. The end products of general formula (I) generally precipitate out after the addition of water or of an aqueous mineral acid, for example hydrochloric acid or sulphuric acid, and, after filtration, are purified by recrystallisation or solumn chromatography.

Another preferred method for the preparation of the compounds of general formula (I) consists in the reaction of about equimolar amounts of the amine (VI) and of the acid (V) in an appropriate solvent with about an equivalent amount of a halogenation agent, for example phosphorus trichloride, phosphorus pentachloride or thionyl chloride, at a temperature of from ambient temperature to the reflux temperature of the mixture. Appropriate solvents are, for example, methylene chloride, carbon tetrachloride, diethyl ether, toluene, xylene and chlorobenzene. In general, the product precipitates out of the solution and is obtained by filtration. If necessary, the reaction mixture can be concentrated to a point at which the product precipitates out of the solution. As further condensation agents for this reaction, there can be used, for example, acidic cationic exchangers, sulphonium salts, sulphuric acid halides, 2-halopyridinium salts, phosphonium salts, N,N'-dicyclohexylcarbodiimide and carbonyl-bis-imidazole.

If, instead of the carboxylic acids, there are used the esters thereof, then working is carried out in the presence or absence of special solvents at a temperature of from 20° C. to the boiling temperature of the mixture. There is thereby preferred the reaction of about equimolar amounts of the amine and of the ester in polyphosphoric acid at a temperature of from 50° to 200° C. but is also possible to work in an inert solvent, for example methylene chloride, benzene, toluene or chlorobenzene, best in the presence of somewhat more than one equivalent of a base, for example sodium methanolate or butyl lithium or of sodium hydride, in dimethyl sulphoxide.

If, instead of the carboxylic acid (V), there is used its anhydride, then the reaction can be carried out with the amine (VI) even at somewhat lower temperatures. It is preferred to work in an inert solvent, for example dichloromethane, diethyl ether, benzene or toluene, at a temperature of from ambient temperature to 60° C. The amine and the anhydride are thereby mixed together in approximately equimolar amounts, an exothermal reaction generally commencing. After subsidence, the reaction mixture is gently warmed for some time for completion of the reaction.

If, instead of the carboxylic acid, there is used an acid halide, then it is preferred to work at a temperature of from −10° C. to ambient temperature. It is thereby preferred to proceed in such a manner that, according to Schotten-Baumann, to an aqueous solution of the amine, which also contains a base, for example an alkali metal hydroxide, such as sodium carbonate, or pyridine, there is slowly added dropwise the acid chloride while cooling with ice and the reaction mixture is then left to stand for some time at ambient temperature. This reaction is possible not only in water but also in an organic solvent, for example methylene chloride, diethyl ether, benzene or toluene. The amines can also be acylated almost quantitatively without the use of acid-binding agents by means of carboxylic acid chlorides by boiling the amine and the carboxylic acid chloride in an inert solvent, for example methylene chloride, benzene or toluene, until the ending of the gas evolution, which takes about 1 to 24 hours. If, however, an acid-binding agent, for example triethylamine or pyridine, is added thereto in slight excess, then the reaction already takes place at a temperature of from −10° C. to ambient temperature.

The compounds of general formula (I) can also be prepared by converting the carboxylic acids of general formula (V) into their imidazolides, advantageously by reacting the acid with N,N-carbonyldiimidazole, in an organic solvent, for example tetrahydrofuran, toluene, benzene or diethyl ether, converting the carboxylic acid imidazolide into a reactive ester and reacting this with the tetrazolylamine (VI) to give the carboxylic acid tetrazolylamide (I).

Compounds of general formula (V) in which X is an oxygen atom are described, inter alia, in European Patent Specification No. 0,239,907 or can be prepared by the processes described therein.

The preparation of compounds (I) from malonic acids of the general formula (VII) takes place in a similar manner: From (VII) and one mole of carbonyl-bis-imidazole there is formed the monoimidazolide which is reacted with, for example, 4-nitrophenol to give an activated monoester to which is then added one mole of 1H-5-aminotetrazole. Subsequently, the reaction mixture is heated to a temperature of from 50° to 80° C., amide formation and decarboxylation thereby taking place. As solvent, there is here preferably used dimethylformamide or dimethyl sulphoxide.

However, the condensation to give the tetrazolamide can also take place with other condensation agents or with other forms of the mono-activated malonic acids (VII), for example with appropriate carbodiimides.

The preparation of compounds (III) from a protected aminoalkylphenol (VIII) and a halocarboxylic acid tetrazolamide (IX) advantageously takes place in a mixture of aqueous alkali metal hydroxide and ethanol. Other reaction conditions, for example condensation by means of potassium carbonate, in an appropriate solvent, for example butan-2-one, or by means of sodium hydride in dimethylformamide or dimethyl sulphoxide, can also be used. The removal of the protective group $R^3$=benzyl takes place by hydrogenation in an alcohol, for example methanol or ethanol, in the presence of hydrogen chloride (methanolic hydrochloric acid) on palladium-charcoal at a temperature of from 20° to 80° C. and at a pressure of up to 8 bar.

Compounds (III) are obtained by reacting aldehydes of general formula (XII) with nitromethane and subsequent hydrogenation/reduction of the nitrostyrene (XIII). The reaction of (XII) with nitromethane takes place, for example, in such a manner that an aqueous solution of an alkali metal hydroxide is added in the cold to a methanolic solution of the components. Instead of the aqueous solution of an alkali metal hydroxide, there can advantageously also be used ethylenediammonium diacetate as condensation agent. The hydrogenation of the nitrostyrene (XIII) takes place, for example, in glacial acetic acid at an elevated temperature and at a hydrogen pressure of up to 8 bar in the presence of palladium-charcoal.

For the preparation of aminoalkylphenoxymalonic acids of general formula (XVII), a hydroxynitrostyrene (XIV) is condensed with chloromalonic ester and subsequently hyrogenated. The condensation takes place in the cold in the presence of an alkali metal hydroxide. The conditions of the phase transfer reactions are here preferred: reaction of the components in a vigorously stirred mixture of aqueous alkali and an appropriate solvent, for example methylene chloride, in the presence of a quaternary ammonium salt, for example tetrabutylammonium bromide. Not only the chloronitroalkylphenoxymalonic ester (XVIII) resulting in the case of the use of one mole of alkali but also the nitrostyreneoxymalonic acid ester resulting in the case of the use of two moles of alkali can be hydrogenated to give the compounds (XVII). The hydrogenation of (XVIII) is carried out either in two stages (first with Pd/C for the removal of the chlorine atom and then with Raney nickel for the reduction of the nitro group) or, with the use of a higher pressure and of a higher temperature, in one stage with Pd/C.

For the preparation of compounds (XVII) in which n can have any desired value, the reaction of N-protected aminoalkylphenols of general formula (XXI) with halomalonic esters and subsequent splitting off of the protective group is especially preferred. For the condensation of (XXI) with halomalonic esters, the phase transfer catalysis is here also especially preferred. However, there can be used all other processes appropriate for the phenyl ether formation, for example the reaction by means of potassium carbonate/butan-2-one or by means of sodium hydride in dimethylformamide or dimethyl sulphoxide. When $Z^1Z^2N$-represents a benzylamino, dibenzylamino or benzyloxycarbonylamino radical, the protective group can be removed by hydrogenation. If it is an acetylamino radical, then hydrolysis is carried out with a dilute aqueous solution of an alkali metal hydroxide.

The conversion of compounds of general formula (I) into other compounds of general formula (I) can take place according to conventional methods.

If, for example, A is a carbonyl group, then all conventional reduction processes can be used for the conversion into a hydroxyl group.

Reduction with complex borohydrides, for example with sodium borohydride, is preferred, in which case protic solvents, for example water, (aqueous) alcohols or aqueous dioxan can be used as reaction medium. In the case of the absence of other reducible groups, the reduction can also be carried out with complex aluminium hydrides, for example lithium aluminium hydride or diisobutyl aluminium hydride (DIBAL), in which case aprotic solvents, for example diethyl ether, tetrahydrofuran or dioxan, can here again be used as reaction medium. However, the carbonyl reduction can also take place with catalytically activated hydrogen, for example using hydrogen/Raney nickel, or by reaction with nickel-aluminium alloy in an aqueous alkali.

For the preparation of salts with physiologically acceptable organic and inorganic bases, for example sodium hydroxide, potassium hydroxide, calcium hydroxide, ammonium hydroxide, methylglucamine, morpholine, triethylamine or ethanolamine, the compounds of general formula (I) are reacted with appropriate bases. Mixtures of the acidic compounds with an appropriate alkali metal carbonate or hydrogen carbonate can also be used.

For the preparation of pharmaceutical compositions, the compounds of general formula (I) are mixed in known manner with appropriate pharmaceutical carrier substances, aroma, flavouring and colouring agents and formed, for example, into tablets or dragees or, with the addition of appropriate adjuvants, suspended or dissolved in water or an oil, for example olive oil.

The compounds of general formula (I) can be administered orally or parenterally in liquid or solid form. As injection medium, it is preferred to use water which contains the stabilising agents, solubilising agents and/or buffers conventional in the case of injection solutions. Additives of this type include, for example, tartrate and borate buffers, ethanol, dimethyl sulphoxide, complex formers (such as ethylenediamine-tetraacetic acid), high molecular weight polymers (such as liquid polyethylene oxide) for viscosity regulation and polyethylene derivatives of sorbite anhydrides.

Solid carrier materials can be, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetaable fats and solid high molecular weight polymers (such as polyethylene glycols). Compositions which are suitable for oral administration can, if desired, contain sweetening and flavouring agents.

The dosage administered depends upon the age, the state of health and the weight of the recipient, the extent of the disease, the nature of further treatments possibly carried out simultaneously, the frequency of the treatments and the nature of the desired action. The daily dose of the active compound usually amounts to from 0.1 to 50 mg./kg. of body weight. Normally, 0.5 to 40 and preferably 1.0 to 20 mg./kg. in one or more administrations per day are effective in order to obtain the desired results.

Preferred in the meaning of the present invention are, apart from the compounds of general formula (I) mentioned in the Examples and the salts thereof, also the following:

1) 4-[2-(4-trifluoromethylbenzenesulphonamido)-ethyl]-phenylacetic acid (1H-tetrazol-5-yl)-amide
2) 3-[2-(4-trifluoromethylbenzenesulphonamido)-ethyl]-phenoxyacetic acid (1H-tetrazol-5-yl)-amide 3) 3-[2-(4-chlorobenzenesulphonamido)-ethyl]-N-(1H-tetrazol-5-yl)-aniline
4) 4-[2-(4-chlorobenzenesulphonamido)-ethyl]-benzyl-N-(1H-tetrazol-5-yl)-amine
5) 3-[2-(4-chlorobenzenesulphonamido)-ethyl]-benzyl-N-(1H-tetrazol-5-yl)-amine
6) 4-[(4-chlorobenzenesulphonamido)-methyl]-phenoxyacetic acid (1H-tetrazol-5-yl)-amide
7) 3-[(4-fluorobenzenesulphonamido)-methyl]-phenoxyacetic acid (1H-tetrazol-5-yl)-amide
8) 4-[3-(2-chlorobenzenesulphonamido)-propyl]-phenylacetic acid (1H-tetrazol-5-yl)-amide
9) 3-[3-(4-trifluoromethylbenzenesulphonylamido)-propyl]-phenylacetic acid (1H-tetrazol-5-yl)-amide
10) 5-{4-[2-(4-chlorobenzenesulphonamido)-ethyl]-benzene}-1H-tetrazole
11) 5-{3-[2-(4-trifluoromethylbenzenesulphonamido)-ethyl]-benzene}-1H-tetrazole
12) 5-{4-[2-(4-chlorobenzenesulphonamido)-ethyl]-benzoyl}-1H-tetrazole
13) 5-{3-[2-(4-fluorobenzenesulphonamido)-ethyl]-benzoyl}-1H-tetrazole.

Thrombocyte aggregation was investigated by the method of Born to Cross (J. Physiol. 168, 178 (1963)) in platelet-rich plasma of healthy blood donors. To inhibit clotting, the blood was mixed with 3.2% citrate in a ration by volume 1:9.

To induce thrombocyte aggregation, U 46619 (Upjohn & Co., Kalamazoo, Mich., U.S.A.), which is a stable analog of the prostagladin endoperoxide $PHG_2$, was used. U 46619 has been characterized as a selective thromboxane mimetic (Coleman et al., Brit. J. Pharmacol, 68, 127 P., 1980).

The aggregation test was carried out in a 4-channel aggregometer (Profiler ®, of the Bio/Data Co., U.S.A.). The course of the aggregation was followed over a period of 5 minutes. At the end of the test, the degree of aggregation attained was printed out. These values, which were obtained in the presence of different concentrations of the substance being tested, were used for the determination of the $IC_{50}$ value for the TX antagonistic effect. The effectiveness varies inversely with the $IC_{50}$ value. The results are given in the Table below.

Male NMRI mice, with a body weight of 25 g, were used. The test substance was suspended in 1% methylcellulose and administered to the experimental animals with the aid of a stomach tube. The provocation test consisted of injecting a lethal dose (800–1000 /ug/kg) of the thromboxane mimetic (U 46619, Upjohn Co.) rapidly into the tail vein. The duration of the specific antagonistic effect was tested by pretreating the animals with 25 or 1 mg/kg of the different test substances and injecting U 46619 after 4 hours. The survival rate indicates how many of the animals which were used survived the injection of the thromboxane mimetic. The results are given in the Table below.

| Substance Example | Survival Rate of Mouse 25 mg/kg, 4 h in % | Survival Rate of Mouse 1 mg/kg, 4 h in % | Thromboxane Aggregation $IC_{50}$ (μM) |
| --- | --- | --- | --- |
| Nr. 2 | 100 | 100 | 6.0 |
| Nr. 3 | 100 | 20 | 0.2 |
| Nr. 4 | 100 | 80 | 9.0 |
| Nr. 5 | 100 | 80 | 0.9 |
| Nr. 6/III | 100 | 100 | 55.0 |
| Nr. 8 | 100 | 100 | 0.07 |
| Nr. 15 | 100 | 100 | 24.0 |
| Nr. 16 | 100 | 40 | 17.0 |

The following Examples are given for the purpose of illustrating the present invention:

EXAMPLE 1

5-{4-[2-(4-Chlorobenzenesulphonamido)-ethyl]-phenoxymethyl}-1H-tetrazole 3.50 g. (16 mMol) 5-[4-(2-aminoethyl)-phenoxymethyl]-1H-tetrazole and 1.8 g. sodium hydroxide are suspended in 100 ml. water and 3.55 g. (16 mMol) 4-chlorobenzenesulphonyl chloride added thereto at 40° to 50° C. within the course of 30 minutes. The pH value is thereby maintained at 10.5 by the dropwise addition of 5N aqueous sodium hydroxide solution, using a pH meter. After stirring for 1 hour at 70° to 80° C., the reaction mixture is cooled to ambient temperature, acidified and extracted with ethyl acetate. The combined organic phases are again extracted with dilute aqueous sodium hydrogen carbonate solution, acidified and extracted with ethyl acetate. The organic phase is washed with water, dried over anhydrous sodium sulphate and evaporated to dryness. After crystallisation from ethanol, there are obtained 3.50 g. (56% of theory) of colourless crystals; m.p. 136° C.

The starting material can be obtained as follows:

a) N-(Benzyloxycarbonyl)-p-hydroxyphenethylamine 34.25 g. (0.25 mol) tyramine are dissolved in 400 ml. water and 35.5 ml. (0.25 mol) benzyl chloroformate slowly added dropwise thereto. By means of the simultaneous addition of a concentrated aqueous solution of sodium hydrogen carbonate, the pH value is kept at 9 by means of a pH meter control. The resultant precipitate is filtered off with suction, washed with water, taken up in 2N aqueous sodium hydroxide solution and extracted three times with ethyl acetate. The aqueous phase is acidified with 2N hydrochloric acid, extracted three times with ethyl acetate, dried over anhydrous magnesium sulphate and evaporated to dryness. There are obtained 50.30 g. (74% of theory) N-(benzyloxycarbonyl)-p-hydroxyphenethylamine, colourless crystals; m.p. 100°–102° C.

b) 4-[2-(Benzyloxycarbonylamino)-ethyl]-phenoxyacetonitrile 48.82 g. (0.18 mol) of the above-prepared N-(benzyloxycarbonyl)-p-hydroxyphenethylamine are introduced into a sodium ethylate solution freshly prepared from 5.17 g. sodium and 270 ml. ethanol, 11.4 ml. (0.18 mol) chloroacetonitrile are slowly added dropwise thereto and the reaction mixture is heated to the boil. After 5 hours, the solvent·is stripped off, the residue is taken up in diethyl ether, extracted twice with 2N aqueous sodium hydroxide solution, washed neutral, dried over anhydrous sodium sulphate and evaporated to dryness. The oily residue is recrystallised from ligroin/diethyl ether (8:2 v/v). There are obtained 44.74 g. (80% of theory) of the desired product in the form of colourless crystals; m.p. 110°–115° C.

c)

5-{4-[2-(Benzyloxycarboxyamino)-ethyl]-phenoxymethyl}-1H-tetrazole 7.60 g. (25 mMol) of the compound prepared in b), 5.0 g. (77 mMol) sodium azide and 5.30 g. (39 mMol) triethylamine hydrochloride are dissolved in 350 ml. 1-methyl-2-pyrrolidinone and the reaction mixture is stirred for 8 hours at 150° C. After cooling to ambient temperature, the solvent is distilled off at 85° C./16 Torr, the oily residue is taken up in 2N aqueous sodium hydroxide solution and extracted three times with diethyl ether. The aqueous phase is acidified with semi-concentrated hydrochloric acid and extracted three times with ethyl acetate. The combined organic phases are dried over anhydrous magnesium sulphate, the solvent is stripped off and the oily residue is brought to crystallisation with diethyl ether. There are obtained 8.20 g. (93% of theory) of the desired product; colourless crystals; m.p. 95° C. (decomp.).

d) 5-[4-(2-Aminoethyl)-phenoxy]-methyl-1H-tetrazole 8.10 g. (23 mMol) of the tetrazole obtained in c) are dissolved in 400 ml. ethanol and hydrogenated in the presence of 0.5 g. palladium/charcoal (10%) under normal conditions. There are obtained 4.60 g. (91% of theory) of the desired product; colourless crystals; m.p. 167°–168° C.

EXAMPLE 2

3-[2-(4-Chlorobenzenesulphonamido)-ethyl]-phenoxyacetic acid (1H-tetrazol-5-yl)-amide In a manner analogous to that described in Example 1, by the reaction of the appropriate 3-(2-aminoethyl)-phenoxyacetic acid (1H-tetrazol-5-yl)-amide with 4-chlorobenzene sulphochloride, there is obtained the title compound; m.p. 190°–196° C. (decomp.), after crystallisation from glacial acetic acid.

EXAMPLE 3

4-[2-(4-Chlorobenzenesulphonamido)-ethyl]-N-(1H-tetrazole-5-yl)-aniline 3.0 g. (9 mMol) 4-[2-(4-chlorobenzenesulphonamido)-ethyl]-cyanoanilide, 2.42 g. (45 mMole) ammonium chloride and 2.92 g. (45 mMol) sodium azide are dissolved in 225 ml. dry dimethylformamide and the mixture is reacted in an autoclave at 120° C. and 150 bar for 60 hours. After distilling off the solvent, the residue is taken up in ethyl acetate and extracted three times with 2N aqueous sodium hydroxide solution. The aqueous alkaline phases are now acidified with 2N hydrochloric acid (care, protective shield) and extracted three times with ethyl acetate. The combined organic phases are dried over anhydrous sodium sulphate and evaporated to dryness. The residue thus obtained is again dissolved in 2N aqueous sodium hydroxide solution, filtered off from insolubles and acidified with 2N hydrochloric acid. The resultant precipitate is filtered off with suction and dried. After chromatography over silica gel with methylene chloride/methanol (9:1 v/v) as elution agent, there is obtained the title compound in the form of pale pink crystals; m.p. 148.5°–150° C. Yield 2.3 g. (68% of theory). The 4-[2-(4-chlorobenzenesulphonamido)-ethyl]-cyanoanilide used as starting material is obtained as follows:

a) p-Nitrophenethylamine 24.2 g. (0.20 mol) Phenethylamine are carefully mixed in an ice-bath with 125 ml. concentrated sulphuric acid. After stirring for 1 hour, 16.8 g. (0.21 mol) ammonium nitrate in 125 ml. concentrated sulphuric acid are carefully added dropwise thereto at 0° to 5° C. After a further hour, the reaction mixture is poured on to 1.5 liters of ice and the pH adjusted to 9 with a concentrated aqueous solution of ammonium hydroxide. The aqueous phase is extracted several times with diethyl ether, the combined organic phases are dried over anhydrous magnesium sulphate, evaporated to dryness and the residue is distilled. There are obtained 14.5 g. (44% of theory) of a colourless oil; b.p. 110°–115° C./0.01 Torr. $^1$H-NMR (60 MHz, CDCl$_3$, ppm): $\delta = 2.99$ (q, 2H, J=2.0 Hz, CH$_2$); 3.05 (t, 2H, J=2.0 Hz, CH$_2$).

b)

4-[2-(4-Chlorobenzenesulphonamido)-ethyl]-nitrobenzene 14.1 g. (85 mMol) of the above-obtained p-nitrophenethylamine and 34 ml. (340 mMol) triethylamine are dissolved in 170 ml. methylene chloride and 17.9 g. (85 mMol) p-chlorobenzenesulphonic acid chloride in 170 ml. methylene chloride added dropwise thereto at 0° to 5° C. within the course of 1 hour. After stirring for a further hour at 0° C., the reaction mixture is allowed to warm up to ambient temperature. It is then poured on to ice, mixed with 2N hydrochloric acid and shaken out with methylene chloride. The organic phase is washed neutral, dried over anhydrous magnesium sulphate and evaporated to dryness. The oily residue is chromatographed over silica gel with ligroin/ethyl acetate/glacial acetic acid (1.5:1.0:0.006 v/v/v) as elution agent. There are obtained 10.2 g. (35% of theory) of the desired compound in the form of a colourless oil. $^1$H-NMR (60 MHz, d$_6$-DMSO, ppm): $\delta = 2.7$–3.1 (m, 5H, CH$_2$, NH); 7.35 and 8.10 (AB system 2d, J=9.5 Hz, 4H); 7.55 and 7.75 (AB system, 2d, J=10 Hz, 4H).

c) 4-[2-(4-Chlorobenzenesulphonamido)-ethyl]-aniline 10.0 g. (29 mMol) of the product obtained in b) are dissolved in 600 ml. glacial acetic acid, mixed with 1.5 g. palladium/charcoal (10%) and hydrogenated under normal pressure and at ambient temperature. After filtration, the solvent is stripped off and the residue is taken up in diethyl ether and extracted three times with 2N hydrochloric acid. The combined aqueous phases are rendered alkaline with 2N aqueous sodium hydroxide solution and extracted three times with ethyl acetate. The combined organic phases are dried over anhydrous magnesium sulphate and evaporated to dryness. The oily residue is heated in diethyl ether and the precipitate obtained is filtered off with suction. There are obtained 5.20 g. (58% of theory) of the amino compound in the form of colourless crystals; m.p. 137°–140° C.

d)

4-[2-(4-Chlorobenzenesulphonamido)-ethyl]-cyanoanilide

To a solution of 1.71 g. (16 mMol) cyanogen bromide and 4.90 g. (16 mMol) of the above-obtained 4-[2-(4-chlorobenzenesulphonamido)-ethyl]-aniline in 500 ml. toluene are added 32 ml. (32 mMol) of a 1N sodium ethylate solution and the reaction mixture is stirred for 4 hours at ambient temperature. The resultant precipitate is filtered off, washed with toluene and the toluene phase evaporated to dryness. The oily residue is now mixed with distilled water, rendered alkaline with 10N aqueous sodium hydroxide solution, the resultant precipitate is sharply filtered off with suction and washed with water. From ethanol, there are obtained 3.40 g. (63% of theory) of the desired product in the form of pale yellow crystals; m.p. 137°–140° C.

EXAMPLE 4

4-[2-(4-Chlorobenzenesulphonamido)-ethyl]-phenoxyacetic acid (1H-tetrazol-5-yl)-amide To a suspension of 7.30 g. (20 mMol) 4-[2-(4-chlorobenzenesulphonamido)-ethyl]-phenoxyacetic acid (preparation see European Patent Specification No. 0,239,907) and 2.20 ml. 4-methylmorpholine in 60 ml. dry methylene chloride is added dropwise at −10° C. 2.76 g. (20 mMol) isobutyl chloroformate, dissolved in 40 ml. dry methylene chloride, within the course of 15 minutes. After a further 15 minutes, a solution of 3.06 g. (20 mMol) 5-amino-1,2,3,4-tetrazole and 20 ml. dimethylformamide are added dropwise thereto within the course of 15 minutes. After stirring for 1 hour at −10° C., the reaction mixture is allowed to come to ambient temperature overnight, the solvent is distilled off, the oily residue is taken up in ethyl acetate and shaken out with 2N aqueous sodium hydroxide solution. The aqueous alkaline phases are acidified with 2N sulphuric acid and the resultant precipitate is filtered off with suction and thoroughly washed with water. After crystallisation from ethanol, there are obtained 4.20 g. (48% of theory) of colourless crystals; m.p. 227.5°–229.5° C.

EXAMPLE 5

4-[2-(4-Chlorobenzenesulphonamido)-ethyl]-phenylacetic acid (1H-tetrazol-5-yl)-amide To a suspension of 2.0 g. (5 mMol) 4-[2-(4-chlorobenzenesulphonamido)-ethyl]-phenylacetic acid imidazolide in 5 ml. dimethyl sulphoxide is added 0.7 g. (5 mMol) 4-nitrophenol, the reaction mixture is stirred for 10 minutes and thereby warmed up until a clear solution has formed. To this is added 0.425 g. (5 mMol) 5-aminotetrazole, stirred for 30 minutes at 90° C., cooled to ambient temperature and the reaction mixture then poured into water. The precipitate obtained is filtered off, washed with water and recrystallised from ethanol. There is obtained 1.50 g. (72% of theory) of the title compound in the form of colourless crystals; m.p. 248° C.

The 4-[2-(4-chlorobenzenesulphonamido)-ethyl]-phenylacetic acid imidazolide used as starting material is obtained as follows: 7.10 g. (20 mMol) 4-[2-(4-chlorobenzenesulphonamido)-ethyl]-phenylacetic acid in 50 ml. tetrahydrofuran are mixed at 50° C. with 3.25 g. (20 mMol) N,N-carbonyldiimidazole and the precipitate obtained is filtered off after 15 minutes and washed with diethyl ether. There are obtained 5.30 g. (66% of theory) of the desired product in the form of colourless crystals; m.p. 168°–170° C.

EXAMPLE 6

I)
4-Oxo-4-{4-[2-(benzenesulphonamido)-ethyl]-phenyl}-butyric acid (1H-tetrazol-5-yl)-amide Analogously to Example 3, from 7.20 g. (20 mMol) 4-oxo-4-{4-[2-(benzenesulphonamido)-ethyl]-phenyl}-butyric acid and 4.11 g. (40 mMol) 5-amino-1,2,3,4-tetrazole, there are obtained 2.20 g. (26% of theory) of the title compound in the form of colourless crystals; m.p. 241°–242° C.

The following compounds are prepared in a corresponding manner:

II)
4-Oxo-4-{4-[2-(4-chlorobenzenesulphonamido)-ethyl]-phenyl}-butyric acid (1H-tetrazol-5-yl)-amide Yield: 75% of theory; colourless crystals; m.p. 238°–239° C. (recrystallised from dimethylformamide/water).

III)
4-Oxo-4-{4-[2-(4-bromobenzenesulphonamido)-ethyl]-phenyl}-butyric acid (1H-tetrazol-5-yl)-amide Yield: 67% of theory, colourless crystals, m.p. 239°–239.5° C. (recrystallised from dimethylformamide/water).

IV)
4-Oxo-4-{4-[2-(4-cyanobenzenesulphonamido)-ethyl]-phenyl}-butyric acid (1H-tetrazol-5-yl)-amide Yield: 59% of theory; colourless crystals; m.p. 238°–239° C. (recrystallised from dimethylformamide/water).

v)
4-Oxo-4-{4-[2-(p-tolylsulphonamido)-ethyl]-phenyl}-butyric acid (1H-tetrazol-5-yl)-amide Yield: 63% of theory; colourless crystals; m.p. 222°–223° C. (recrystallised from methanol).

The 4-oxo-4-{4-[2-(4-R-benzenesulphonamido)-ethyl]-phenyl}-butyric acid used as starting material can be prepared as follows:

a) N-Acetylphenethylamine 350 ml. (3.14 mol) Acetic anhydride are added dropwise within the course of 50 minutes to a solution of 376 ml. (3.0 mol) phenethylamine in 1.5 liters toluene, the temperature thereby increasing to 68° C. The reaction mixture is heated under reflux for 1 hour, the toluene is evaporated off in a high vacuum and the residue is distilled at 1.5 mm.Hg. Yield 475 g. (97% of theory); b.p. 162°–166° C./1.5 mm.Hg; m.p. 50°–52° C.

b) Methyl 4-oxo-4-{4-[2-(N-acetylamino)-ethyl]-phenyl}-butyrate 272.7 g. (2.04 mol) aluminium chloride are introduced portionwise at 0° C. into a solution of 110.97 g. (0.68 mol) N-acetylphenethylamine and 93 ml. (0.75 mol) succinic acid methyl ester chloride in 1200 ml. anhydrous methylene chloride, the reaction mixture is further stirred for 1 hour at 0° C. and then warmed to ambient temperature. The reaction mixture is poured into hydrochloric acid/ice water, the organic phase is separated off, dried over anhydrous magnesium sulphate and evaporated. The residue is stirred up with hot diethyl ether, filtered off with suction and afterwashed with a little cold diethyl ether. Yield 154 g. (82% of theory); colourless crystals; m.p. 119.5° C.

c) 4-Oxo-4-[4-(aminoethyl)-phenyl]-butyric acid 130 g. (0.47 mol) of the compound from b) in 1200 ml. 6N hydrochloric acid are heated under reflux for 8 hours, cooled to 0° C. and the precipitate obtained is filtered off with suction. Yield: 103.1 g. (99.6% of theory); colourless crystals; m.p. 234°–235° C. (recrystallised from ethanol).

d)
4-Oxo-4-{4-[2-(4-R-benzenesulphonamido)-ethyl]-phenyl}-butyric acid 40 mMol 4-R-benzenesulphonic acid chloride are added within the course of 30 minutes to 8.85 g. (40 mMol) of the compound from c) and the pH value maintained at 10.5 by the dropwise addition of 5N aqueous sodium hydroxide solution. After completion of the addition, stirring is continued for 1 hour at 70° to 80° C. The reaction mixture is then cooled and extracted with diethyl ether. The aqueous phase is then adjusted to a pH of 4 to 5, extracted three times with ethyl acetate, the organic phase is dried over anhydrous magnesium sulphate and the solvent is distilled off. The residue is recrystallised from diethyl ether.
1) R=H: yield 9.9 g. (69% of theory); colourless crystals; m.p. 156°–158° C.
2) R=Cl: yield 11.1 g. (70% of theory); colourless crystals; m.p. 151°–151.5° C.
3) R=Br: yield 10.3 g. (59% of theory); colourless crystals; m.p. 150°–152° C.
4) R=CN: yield 10.73 g. (69% of theory); colourless crystals; m.p. 148°–150° C.

p-Cyanobenzenesulphonic acid chloride is obtained by reacting 4-sulphonylbenzoic acid with phosphorus pentachloride (J. pharm. Soc. Japan, 69, 417/1949; C.A., 1950, 1924).
5) R=CH$_3$: yield 11.6 g. (77% of theory); pale yellow crystals; m.p. 133°–135° C.

EXAMPLE 7

4-Hydroxy-4-{4-[2-(4-chlorobenzenesulphonamido)-ethyl]-phenyl}-butyric acid (1H-tetrazol-5-yl)-amide A solution of 0.30 g. (80 mMol) lithium borohydride in 3.2 ml. 0.2N aqueous sodium hydroxide solution is added dropwise at 0° C. to a suspension of 3.7 g. (80 mMol) of the keto compound from Example 6 II) in 80 ml. 0.6% aqueous sodium hydroxide solution within the course of 15 minutes. The reaction mixture is stirred for 30 minutes at ambient temperature, then for 2 hours at 60° C., cooled and washed with diethyl ether. The aqueous phase is acidified with 5N hydrochloric acid, extracted with ethyl acetate, dried over anhydrous magnesium sulphate and evaporated to dryness. The residue is recrystallised from dimethylformamide/water. There are obtained 2.8 g. (75% of theory) of the title compound in the form of colourless crystals; m.p. 194.5°–195.5° C.

EXAMPLE 8

5-{4-[2-(4-Chlorobenzenesulphonamido)-ethyl]-phenylmethyl}-1H-tetrazole 4.62 g. (13.8 mMol) 4-[2-(4-chlorobenzenesulphonamido)-ethyl]-phenylacetonitrile, 2.94 g. (21.3 mMol) triethylammonium chloride and 2.77 g. (42.6 mMol) sodium azide in 150 ml. 1-methylpyrrolidone are heated to 150° C. for 6 hours. The 1-methylpyrrolidone is subsequently distilled off in a high vacuum at 80° to 90° C., the residue is dissolved in dilute aqueous sodium hydroxide solution and extracted three times with ethyl acetate. The aqueous phase is acidified with hydrochloric acid, also extracted three times with ethyl acetate, the extracts are dried over anhydrous sodium sulphate and, after treating with active charcoal, evaporated to dryness. The residue is taken up in an aqueous solution of sodium hydrogen carbonate, extracted with ethyl acetate and acidified, the product thereby crystallising out. There is obtained 1.5 g. (29% of theory) of the title compound in the form of colourless crystals; m.p. 168°–169° C.

The 4-[2-(4-chlorobenzenesulphonamido)-ethyl]-phenylacetonitrile used as starting material is obtained as follows:

a) Ethyl 4-[2-(4-chlorobenzenesulphonamido)-ethyl]-benzoate

A suspension of 11.5 g. (50 mMol) ethyl 4-(2-aminoethyl)-benzoate hydrochloride (J.A.C.S., 65, 2281, 2284/1943) and 12.65 g. (125 mMol) triethylamine in 150 ml. methylene chloride is stirred for 30 minutes at ambient temperature, cooled to 0° C. and a solution of 11.55 g. (50 mMol) 4-chlorobenzenesulphonic acid chloride in 50 ml. methylene chloride slowly added dropwise thereto. After ending of the reaction, the reaction mixture is extracted twice with dilute hydrochloric acid, washed with water and the organic phase then dried over anhydrous sodium sulphate. After evaporation of the solvent, there are obtained 11.4 g. (62% of theory) of colourless crystals; m.p. 88° C., after recrystallisation from ethanol.

b) 4-[2-(4-Chlorobenzenesulphonamido)-ethyl]-benzyl alcohol 1.2 g. (30 mMol) lithium aluminium hydride in 100 ml. anhydrous tetrahydrofuran are added dropwise to a suspension of 11.0 g. (30 mMol) of the benzoic acid derivative obtained in a) in 100 ml. anhydrous tetrahydrofuran and the reaction mixture then heated under reflux for 2 hours. The reaction mixture is subsequently hydrolysed with ice water/2N sulphuric acid and the precipitate obtained is filtered off with suction. The yield is 7.0 g. (72% of theory) of colourless crystals; m.p. 145°–146° C., after recrystallisation from ethanol.

c)
4-[2-(4-Chlorobenzenesulphonamido)-ethyl]-benzylchloride 5.5 g. (16.9 mMol) of the benzyl alcohol obtained in b) are dissolved in 30 ml. benzene, 3.0 g. (25 mMol) thionyl chloride and 5 drops of pyridine are added thereto and the reaction mixture is heated under reflux for 30 minutes. The reaction mixture is evaporated to dryness and the residue is recrystallised from isohexane/diethyl ether. The yield is 5.6 g. (95% of theory) of colourless crystals; m.p. 96°–98° C.

d)
4-[2-(4-Chlorobenzenesulphonamido)-ethyl]-benzylcyanide 5.43 g. (15.8 mMol) of the benzyl chloride obtained in c) and 1.18 g. (24 mMol) sodium cyanide are dissolved in 40 ml. 90% ethanol and the reaction mixture is stirred for 2 hours at 80° C. The solvent is now distilled off and the residue is mixed with water and extracted with methylene chloride. There are obtained 5.2 g. (99% of theory) of a colourless oil.

$^1$H-NMR (300 MHz, d$_6$-DMSO, ppm): δ=2.70 (t, J=6 Hz, 2H, CH$_2$); 3.00 (q, J=6 Hz, 2H, CH$_2$); 3.25 (s, 2H, CH$_2$—CN); 7.15 and 7.23 (2d, AA'BB' system, J=9 Hz, 4H̄, p-phenylene); 7.62 and 7.76 (2d, AA'BB' system, J=10 Hz, 4H, p-chlorophenylene).

IR (cm$^{-1}$): V$_{N-H}$=3249 (s); V$_{C-N}$=2200 (w).

EXAMPLE 9

5-{4-[2-(4-Chlorobenzenesulphonamido)-ethyl]-phenyl}-pentanoic acid (1H-tetrazol-5-yl)-amide The preparation takes place analogously to Example 5: 2.9 g. (17.7 mMol) carbonyldiimidazole are added portionwise to a solution of 7.0 g. (17.7 mMol) 5-{4-[2-(4-chlorobenzenesulphonamido)-ethyl]-phenyl}-pentanoic acid in 100 ml. anhydrous tetrahydrofuran and then 2.5 g. (17.7 mMol) nitrophenol and, after 10 minutes, 1.5 g. (17.7 mMol) aminotetrazole. The reaction mixture is heated to 60° C. for 2 hours, the tetrahydrofuran is evaporated off and the residue is stirred with water. The precipitate obtained is filtered off with suction and recrystallised from ethanol. Yield 3.7 g. (45% of theory) of colourless crystals; m.p. 226° C.

The 5-{4-[2-(4-chlorobenzenesulphonamido)-ethyl]-phenyl}-pentanoic acid used as starting material is obtained as follows:

a) Methyl 5-oxo-5-[4-(2-acetaminoethyl)-phenyl]-pentanoate (cf. C.A., 54, 22474e)

To a solution of 26.9 g. (0.165 mol) acetylphenethylamine (preparation see J. Am. Pharm. Assoc., 47, 353/1958) in 300 ml. methylene chloride is added dropwise first 30.0 g. (0.182 mol) glutaric acid methyl ester chloride and then 66.1 g. (0.495 mol) aluminium chloride are added portionwise thereto at 0° to 5° C. The reaction mixture is further stirred for 1 hour at 0° C., then allowed to warm up to ambient temperature and after 4 hours the reaction mixture is poured on to ice/-hydrochloric acid. The organic phase is separated off, washed neutral with water and dried over anhydrous sodium sulphate. After stripping off the solvent, there are obtained 34 g. (71% of theory) of colourless crystals; m.p. 107°–108° C., after recrystallisation from ethyl acetate.

b) Methyl 5-[4-(2-acetaminoethyl)-phenyl]-pentanoate

In a hydrogenation apparatus, 9.0 g. (31 mMol) of the ketone obtained in a) are dissolved in 100 ml. methanol and hydrogenated at ambient temperature and 5 bar pressure. As catalyst, there is used 1.0 g. 10% Pd/C and 1 ml. concentrated hydrochloric acid. After taking up 1.2 liters of hydrogen, the reaction is stopped, the catalyst is filtered off with suction and the methanol is distilled off. The residue is taken up in diethyl ether, washed with 2N aqueous sodium hydrogen carbonate solution, dried over anhydrous sodium sulphate and evaporated. There are obtained 6.6 g. (77% of theory) of colourless crystals; m.p. 57°–59° C., after recrystallisation from ligroin.

c) Ethyl 5-[4-(2-aminoethyl)-phenyl]-pentanoate

A solution of 6.4 g. (23.1 mMol) of the acetamino compound obtained in b) in 40 ml. 6N hydrochloric acid is heated under reflux for 8 hours. Upon cooling, 5-[4-(2-aminoethyl)-phenyl]-pentanoic acid precipitates out as the hydrochloride. It is filtered off with suction, after-washed with 2N hydrochloric acid and dried over potassium hydroxide. There are obtained 2.8 g. (47% of theory) of colourless crystals; m.p. 210°–213° C.

$^1$H-NMR (300 MHz, d$_6$-DMSO, ppm, after shaking with D$_2$O): δ=1.20 (t, J=6.1 Hz, 3H, CH$_3$); 1.55 (m, 4H, CH$_2$—CH$_2$); 2.30 (t, J=7 Hz, 2H, CH$_2$—COOEt); 2.55 (t, J=6 Hz, 2H, Ph—CH$_2$); 2.90 (q, J=6 Hz, 2H, CH$_2$); 3.05 (t, J=9 Hz, 2H, Ph—CH$_2$); 4.05 (q, J=6.5 Hz, 2H, CH$_2$); 7.15 and 7.17 (2d, J=8 Hz, AA'BB' system 4H, p-phenylene).

For conversion into the ethyl ester, 2.7 g. (10.5 mMol) of the product are dissolved in 100 ml. ethanol and gaseous hydrogen chloride is passed through the solution for about 2 hours. The solvent is distilled off, the residue is mixed with ice-cold, dilute aqueous sodium hydroxide solution and extracted with diethyl ether. The organic phase is again washed with water, dried over anhydrous sodium sulphate and evaporated. There are obtained 2.4 g. (92% of theory) of the free base in the form of a colourless oil. It is unstable and must be quickly further worked up.

IR (cm$^{-1}$): V$_{C-O}$=1730 (s); V$_{C-H}$=2840−3000 (s); V$_{N-H}$=3350 (m).

d) 5-{4-[2-(4-Chlorobenzenesulphonamido)-ethyl]-phenyl}-pentanoic acid

To a suspension of 6.0 g. (21 mMol) of the aminopentanoic acid from c) and 5.3 g. (52.5 mMol) triethylamine in 100 ml. methylene chloride are added portionwise at 0° C. 4.4 g. (21 mMol) 4-chlorobenzenesulphonic acid chloride, followed by stirring for 1 hour at 0° C. and for 1 hour at ambient temperature. The reaction mixture is shaken out with 2N hydrochloric acid and the organic phase is dried over anhydrous sodium sulphate and evaporated. There are obtained 9.8 g. of the ester in the form of a pale yellow oil which is converted into the free acid by heating with 30 ml. 2N aqueous sodium hydroxide solution in 30 ml. methanol to 50° C. and subsequent acidification with concentrated hydrochloric acid. The yield is 7.4 g. (85% of theory) of colourless crystals; m.p. 118°–120° C.

EXAMPLE 10

3-[2-(4-Chlorobenzenesulphonamido)-ethyl]-phenoxyacetic acid (1H-tetrazol-5-yl)-amide To a solution of 300 ml. anhydrous tetrahydrofuran and 2.07 g. (5 mMol) of the malonic acid obtained according to Example 10 e) is added 1.03 g. (5 mMol) dicyclohexyl-carbodiimide, the reaction mixture is stirred for 10 minutes and then 0.51 g. (5 mMol) 5-amino-1H-tetrazole hydrate added thereto. The reaction mixture is subsequently stirred for 3 hours at 50° C., evaporated in a vacuum and sodium carbonate (10 mMol) in the form of a 2N aqueous solution added to the residue. The reaction mixture is stirred for 10 minutes, dicyclohexylurea is filtered off and the filtrate is acidified. After filtering off with suction, the product is dried and recrystallised from 95% ethanol. Yield 1.89 g. (87% of theory); m.p. 184°–186° C.

The compound can also be prepared according to the following process:

To a solution with a temperature of 45° C. of 200 ml. dimethyl sulphoxide and 2.07 g. (5 mMol) of the malonic acid obtained according to Example 10 e) is added 0.81 g. (5 mMol) carbonyl-bis-imidazole, the reaction mixture is stirred for 10 minutes, 0.70 g. (5 mMol) 5- nitrophenol and 0.425 g. (5 mMol) anhydrous 5-amino-1H-tetrazole are introduced and the reaction mixture kept for 2 hours at 80° C. Thereafter, it is cooled, stirred into 2N hydrochloric acid, filtered off with suction and, after drying, recrystallised from 95% ethanol. Yield 1.55 g. (71% of theory); m.p. 186°–187° C.

The {3-[2-(4-chlorobenzenesulphonamido)-ethyl]-phenoxy}-malonic acid used as starting material is prepared in the following way:

a) 3-(2-Benzylaminoethyl)-phenol

A mixture of 17.6 g. (79.6 mMol) tetrahydropyran-2-yl ether of 3-(2-aminoethyl)-phenol, 150 ml. ethanol and 8.9 g. (83.5 mMol) benzaldehyde is stirred for 1 hour at ambient temperature, 3.5 g. (92 mMol) sodium borohydride are added thereto at 0° C. with vigorous stirring and the reaction allowed to continue for 1 hour at 0° C. and for 1 hour at ambient temperature. The reaction mixture is then evaporated in a vacuum and the residue mixed with diethyl ether and water. After shaking up, the ethereal phase is separated off, dried with anhydrous sodium sulphate and mixed dropwise with concentrated sulphuric acid. The precipitated sulphate is dissolved in water, some 2N hydrochloric acid is added thereto, followed by heating on a waterbath for 10 minutes and cooling. By the addition of sodium carbonate, the base is liberated. It is extracted with diethyl ether, the ethereal solution is dried with anhydrous sodium sulphate and evaporated. Yield 15.0 g. (83% of theory); m.p. 86°–88° C.

$^1$H-NMR (300 MHz, d$_6$-DMSO, ppm): δ=2.62–2.75 (m, 4H, CH$_2$CH$_2$).

b) [3-(2-Benzylaminoethyl)-phenoxy]-malonic acid

To a solution of 8.0 g. (35.2 mMol) 3-(2-benzylaminoethyl)-phenol and 100 ml. ethanol there are added 35.2 mMol sodium methylate in the form of a methanolic solution and thereafter 6.8 g. (35.2 mMol) diethyl chloromalonate. After stirring for 4 hours, the reaction mixture is evaporated. 50 ml. Diethyl ether are added to the residue, as well as ice-cold 1N aqueous sodium hydroxide solution, shaken up and the ethereal phase is separated off. After drying over anhydrous sodium sulphate, the sulphate is precipitated from it by the dropwise addition of concentrated sulphuric acid, which is filtered off with suction and washed with diethyl ether. The product is very hygroscopic and is obtained in the form of a somewhat greasy mass. Yield 11.7 g. (74% of theory).

$^1$H-NMR (300 MHz, d$_6$-DMSO, ppm): δ=2.90–2.98 and 3.11–3.22 (2m, each 2H, CH$_2$); 5.62 (s, 1H, OC$\underline{H}$).

c) Diethyl [3-(2-aminoethyl)-phenoxy]-malonate sulphate

The compound obtained according to b) is hydrogenated in ethanol at 60° C. and normal pressure in the presence of 10% palladium on charcoal until the necessary amount of hydrogen has been taken up. After removing the catalyst by suction filtration, the filtrate is evaporated. There is obtained a quantitative yield of the sulphate in the form of a colourless oil.

$^1$H-NMR (300 MHz, d$_6$-DMSO, ppm); δ=2.91 (t, J=7 Hz, 2H, CH$_2$); 3.11 (t, J=7 Hz, 2H, CH$_2$); 5.54 (s, 1H, OC$\underline{H}$).

d) Diethyl {3-[2-(4-chlorobenzenesulphonylamino)ethyl]-phenoxy}-malonate

This compound is obtained in a manner analogous to Example 3 b) from diethyl [3-(2-aminoethyl)-phenoxy]-malonate and 4-chlorobenzenesulphonyl chloride. Yield 72% of theory; m.p. 60°–62° C.

e) {3-[2-(4-Chlorobenzenesulphonylamino)-ethyl]-phenoxy}-malonic acid

A mixture of 12.0 g. (25.5 mMol) of the diethyl ester obtained according to d), 120 ml. 2N aqueous sodium hydroxide solution and 120 ml. methanol is stirred for 2 hours at 50° C. The methanol is then evaporated off in a vacuum and acidified with concentrated hydrochloric acid. Washing with water (the compound is readily soluble in water) and drying gives the desired product in the form of colourless crystals. Yield 7.2 g. (68% of theory); m.p. 183° C. (decomp.).

EXAMPLE 11

3-[2-(4-Chlorobenzenesulphonamido)-ethyl]-phenoxyacetic acid (1H-tetrazol-5-yl)-amide Analogously to Example 5, from 8.39 g. (20 mMol) 3-[2-(4-chlorobenzenesulphonamido)-ethyl]-phenoxyacetic acid imidazolide, there is obtained 1.60 g. (18% of theory) of the title compound in the form of colourless crystals; m.p. 186° C., after recrystallisation from methanol.

The imidazolide used as starting material is obtained from 7.4 g. (20 mMol) 3-[2-(4-chlorobenzenesulphonamido)-ethyl]-phenoxyacetic acid and 3.25 g. (20 mMol) carbonyldiimidazole in quantitative yield.

EXAMPLE 12

3-[2-(4-Chlorobenzenesulphonamido)-ethyl]-phenoxyacetic acid (1H-tetrazol-5-yl)-amide To a suspension of 10.0 g. (33.5 mMol) 3-(2-aminoethyl)-phenoxyacetic acid (1H-tetrazol-5-yl)-amide hydrochloride (see f) below) and 250 ml. water, there is added sufficient 2N aqueous sodium hydroxide solution to give a pH value of 10. 7.3 g. (34.6 mMol) 4-chlorobenzenesulphochloride are then added thereto, taking care by the controlled addition of 2N aqueous sodium hydroxide solution that the pH value remains at 10.0 until the end of the reaction. The reaction mixture is then added dropwise to an ice-hydrochloric acid mixture and the precipitate obtained is filtered off with suction. After washing with water, drying in a desiccator and recrystallising from glacial acetic acid, there are obtained 12.1 g. (82.7% of theory) of the desired product; m.p. 190°–199° C. (slow decomposition). The product is identical to that obtained according to Example 10.

The 3-(2-aminoethyl)-phenoxyacetic acid (1H-tetrazol-5-yl)-amide hydrochloride used as starting material is obtained as follows:

a) {3-[2-Benzyloxycarbonylamino)-ethyl]-phenyl}-tetrahydropyranyl ether

To a suspension of 25.0 g. (113 mMol) [3-(2-aminoethyl)-phenyl]-tetrahydropyranyl ether, 200 ml. methylene chloride and 60 ml. 2N aqueous sodium hydroxide solution is slowly added, while cooling in an ice-bath and stirring, a solution of 118 mMol benzyl chloroformate and 50 ml. methylene chloride. The reaction mixture is subsequently stirred for 1 hour at the temperature of the icebath and thereafter for 1 hour at ambient temperature, whereafter the phases are separated. The methylene chloride phase is washed twice with water, dried over anhydrous sodium sulphate and subsequently evaporated in a vacuum. The product is obtained in quantitative yield in the form of a colourless oil.

b) 3-[2-(Benzyloxycarbonylamino)-ethyl]-phenol

A mixture of 16.8 g. (47.3 mMol) {3-[2-(benzyloxycarbonylamino)-ethyl]-phenyl}-tetrahydropyranyl ether, 80 ml. ethanol and 3 g. Amberlyst is stirred for 2 hours at ambient temperature, then filtered and evaporated. The last traces of ethanol are removed by blowing in air with the application of a slight vacuum at 70° C. The product is obtained in the form of a colourless oil. Yield quantitative.

c) Ethyl 3-[2-(Benzyloxycarbonylamino)-ethyl]-phenoxyacetate

A suspension of 12.79 g. (47.1 mMol) 3-[2-(benzyloxycarbonylamino)-ethyl]-phenol, 120 ml. butan-2-one and 19.5 g. pulverised potassium carbonate is maintained at reflux temperature for 1 hour, then cooled, 200 mg. pulverised potassium iodide and 9.12 g. (51.9 mMol) ethyl bromoacetate added thereto and the reaction mixture stirred for 18 hours at 90° C. Subsequently, it is filtered off with suction and the filter cake is washed with hot butan-2-one. The combined butanone phases are evaporated, the oily residue is taken up in diethyl ether and the ethereal phase is extracted twice with ice-cold 2N aqueous sodium hydroxide solution, and thereafter with ice water. After drying with anhydrous sodium sulphate, it is evaporated in a vacuum. There are obtained 15.62 g. (93% of theory) of the desired product in the form of a colourless oil.

d) 3-[2-(Benzyloxycarbonylamino)-ethyl]-phenoxyacetic acid

A mixture of 15.55 g. (43.5 mMol) ethyl 3-[2-benzyloxycarbonylamino)-ethyl]-phenoxyacetate, 45 ml. ethanol and 44 ml. 2N aqueous sodium hydroxide solution is stirred for 1 hour at 25° C. then freed from ethanol in a vacuum. The solution remaining behind is diluted with 160 ml. water and extracted three times with diethyl ether. Thereafter, the aqueous phase is acidified with concentrated hydrochloric acid and the oily product which precipitates out is taken up in diethyl ether. The ethereal solution is dried with anhydrous sodium sulphate and evaporated in a vacuum, 13.28 g. (93% of theory) of the desired acid being obtained in the form of a colourless oil.

e) 3-[2-(Benzyloxycarbonylamino)-ethyl]-phenoxyacetic acid (1H-tetrazol-5-yl)-amide To a solution at 40° C. of 13.1 g. (39.8 mMol) 3-[2-(benzyloxycarbonylamino)-ethyl]-phenoxyacetic acid and 130 ml. anhydrous tetrahydrofuran are added 6.48 g. (39.9 mMol) carbonyl-bis-imidazole, followed by stirring for 30 minutes at 40° C. 3.39 g. (39.9 mMol) anhydrous 5-aminotetrazole are then added thereto and allowed to react for 18 hours at 60° C. After distilling off the tetrahydrofuran, there is obtained a colourless oil which is stirred with 130 ml. 2N hydrochloric acid, crystallisation thereby taking place. The crystals are filtered off with suction, triturated with dilute hydrochloric acid, again filtered off with suction and washed with water. After drying in a vacuum at 80° C. over potassium hydroxide and recrystallising from nitromethane, there are obtained 12.7 g. (50.5% of theory) of the desired product; m.p. 164°–167° C.

f) 3-(2-Aminoethyl)-phenoxyacetic acid (1H-tetrazol-5-yl)-amide hydrochloride

A mixture of 7.0 g. (17.7 mMol) 3-[2-benzyloxycarbonylamino)-ethyl]-phenoxyacetic acid (1H-tetrazol-5-yl)-amide, 170 ml. methanol, 55 ml. water, 18 ml. 2N hydrochloric acid and 0.2 g. 10% palladium-charcoal is hydrogenated for 12 hours at 6 bar pressure. The catalyst is then filtered off with suction and the filtrate evaporated. The residue is stirred with an acetone-diethyl ether mixture (1+3 vol.), filtered off with suction and dried. Yield 4.60 g. (86.9% of theory); hydrochloride m.p. 217°–220° C.

EXAMPLE 13

In a manner analogous to that described in Example 12, there is obtained 3-[2-(4-bromobenzenesulphonamido)-ethyl]-phenoxyacetic acid (1H-tetrazol-5-yl)-amide; yield 91% of theory; m.p. 205°–206° C.

EXAMPLE 14

5-3-[2-(4-Chlorobenzenesulphonamido)-ethyl]-phenoxymethyl-1H-tetrazole

A solution of 1.7 g. (4.85 mMol) 3-[2-(4-chlorobenzenesulphonamido)-ethyl]-phenoxyacetonitrile, 1.03 g. (7.48 mMol) triethylamine hydrochloride and 0.97 g. (14.9 mMol) sodium azide in 50 ml. 1-methylpyrrolidone is stirred for 6 hours at 150° C. The solvent is then distilled off in a high vacuum, the residue is taken up in a dilute aqueous solution of sodium hydroxide and extracted with diethyl ether. The aqueous phase is acidified with 6N hydrochloric acid, extracted with ethyl acetate and dried over anhydrous sodium sulphate. After stripping off the solvent, there is obtained 1.19 g. (62% of theory) of colourless crystals; m.p. 100°–102° C.

The precursor is obtained as follows:

a) 3-[2-(4-Chlorobenzenesulphonamido)-ethyl]-phenoxyacetic acid amide

To a solution of 29.7 g. (72 mMol) 3-[2-(4-chlorobenzenesulphonamido)-ethyl]-phenoxymalonic acid (preparation see Example 10 e)) in 150 ml. anhydrous tetrahydrofuran are added 14.8 g. (72 mMol) dicyclohexylcarbodiimide. The reaction mixture is stirred for 10 minutes and then a weak current of ammonia is passed in for about 1 hour. It is then left to stand for 2 hours and filtered. The mother liquor is evaporated and the residue recrystallised from isohexane. There are obtained 18.0 g. (68% of theory) of colourless crystals; m.p. 113° C.

b) 3-[2-(4-Chlorobenzenesulphonamido)-ethyl]-phenoxyacetonitrile

A solution of 15.0 g. (40 mMol) of the acid amide from a) and 12.0 g. (80 mMol) phosphorus pentoxide in 300 ml. toluene is stirred for 3 hours at 110° C., then mixed with water and extracted with ethyl acetate.

After drying over anhydrous sodium sulphate and stripping off the solvent, there are obtained 11.2 g. (79% of theory) of colourless crystals; m.p. 92° C.

EXAMPLE 15

3-[2-(4-Methylbenzenesulphonamido)-ethyl]-phenoxyacetic acid (1H-tetrazol-5-yl)-amide The compound is obtained analogously to Example 10 by reacting 4-methylbenzenesulphonyl chloride with diethyl [3-(2-aminoethyl)-phenoxy]-malonate. Yield 65% of theory of colourless crystals; m.p. 199°–201° C.

EXAMPLE 16

3-[2-(2-Chlorobenzenesulphonamido)-ethyl]-phenoxyacetic acid (1H-tetrazol-5-yl)-amide The compound is also obtained analogously to Example 10. Yield 60% of theory of colourless crystals; m.p. 150°–153° C.

We claim:

1. Compound of the formula:

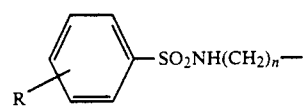

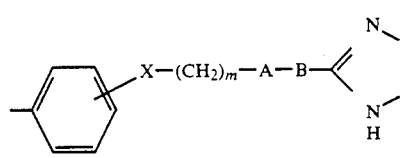

(I)

wherein R is a hydrogen or halogen atom, a cyano group or a $C_1$–$C_6$ alkyl or trifluoromethyl radical, n is 1, 2 or 3, m is 0 or 1 to 5, X is a valency bond, an oxygen atom, a carbonyl group or a —CHOH— group, A is a valency bond or a carbonyl group and B is a valency bonds or an —NH— group; or a physiologically acceptable acid salt or optical isomer thereof.

2. Compound of claim 1, wherein said compound is 3-[2-(4-chlorobenzenesulphonamido)-ethyl]-phenoxyacetic acid (1H-tetrazole-5-yl)-amide.

3. Compound of claim 1, wherein said compound is 4-[2-(4-chlorobenzenesulphonamido)-ethyl]-N-(1H-tetrazole-5-yl)-aniline.

4. Compound of claim 1, wherein said compound is 4-[2-(4-chlorobenzenesulphonamido)-ethyl]-phenoxyacetic acid (1H-tetrazole-5-yl)-amide.

5. Compound of claim 1, wherein said compound is 4-[2-(4-chlorobenzenesulphonamide)-ethyl]-phenylacetic acid (1H-tetrazole-5-yl)-amide.

6. Compound of claim 1, wherein said compound is 4-oxo-4-{4-[2-(4-bromobenzenesulphonamido)-ethyl]-phenyl}-butyric acid (1H-tetrazole-5-yl)-amide.

7. Compound of claim 1 wherein said compound is 5-{4-[2-(4-chlorobenzenesulphonamido)-ethyl]-phenylmethyl}-1H-tetrazole.

8. Compound of claim 1, wherein said compound is 3-[2-(4-methylbenzenesulphonamido)-ethyl]-phenoxyacetic acid (1H-tetrazole-5-yl)-amide.

9. Compound of claim 1, wherein said compound is 3-[2-(2-chlorobenzenesulphonamide)-ethyl]-phenoxyacetic acid (1H-tetrazole-5-yl)-amide.

10. Compound of claim 1, wherein n is 2.

11. Compound of claim 10, wherein A is a carbonyl group and B is an —NH— group.

12. Compound of claim 10, wherein B is an —NH— group.

13. Compound of claim 10, wherein X is a valency bond.

14. Compound of claim 10, wherein X is an oxygen atom.

15. Compound of claim 10, wherein m is 1.

16. Compound of claim 10, wherein R is a halogen atom.

17. Compound of claim 16, wherein the halogen atom is in the 4-position.

18. Compound of claim 16, wherein the halogen atom is a chlorine atom.

19. Compound of claim 1, wherein said compound is selected from the group consisting of 4-[2-(4-trifluoromethylbenzenesulphonamido)-ethyl]-phenylacetic acid (1H-tetrazol-5-yl)-amide, 3-[2-(4-trifluoromethylbenzenesulphonamido)-ethyl]-phenoxyacetic acid (1H-tetrazol-5-yl)-amide, 3-[2-(4-chlorobenzenesulphonamido)-ethyl]-N-(1H-tetrazol-5-yl)-aniline, 4-[2-(4-chlorobenzenesulphonamido)-ethyl]-benzyl-N-(1H-tetrazol-5-yl)-amine, 3-[2-(4-chlorobenzenesulphonamido)-ethyl]-benzyl-N-(1H-tetrazol-5-yl)-amine, 4-[(4-chlorobenzenesulphonamido)-methyl]-phenoxyacetic acid (1H-tetrazol-5-yl)-amide, 3-[(4-fluorobenzenesulphonamido)-methyl]-phenoxyacetic acid (1H-tetrazol-5-yl)-amide, 4-[3-(2-chlorobenzenesulphonamido)-propyl]-phenylacetic acid (1H-tetrazol-5-yl)-amide, 3-[3-(4-trifluoromethylbenzenesulphonylamido)-propyl]-phenylacetic acid (1H-tetrazol-5-yl)-amide, 5-{4-[2-(4-chlorobenzenesulphonamido)-ethyl]-benzene}-1H-tetrazole, 5-{3-[2-(4-trifluoromethylbenzenesulphonamido)-ethyl]-benzene}-1H-tetrazole, 5-{4-[2-(4-chlorobenzenesulphonamido)-ethyl]-benzoyl}-1H-tetrazole, 5-{3-[2-(4-fluorobenzenesulphonamido)-ethyl]-benzoyl}-1H-tetrazole, 5-{4-[2-(4-Chlorobenzenesulphonamido)-ethyl]-phenoxy-methyl}-1H-tetrazole, 4-Oxo-4-{4-[2(benzenesulphonamido)-ethyl]-phenyl}-butyric acid (1H-tetrazol-5-yl)-amide, 4-Oxo-4-{4-[2-(4-chlorobenzenesulphonamido)-ethyl]-phenyl}-butyric acid (1H-tetrazol-5-yl)-amide, 4-Oxo-4-{4-[2-(4-cyanobenzenesulphonamido)-ethyl]-phenyl}-butyric acid (1H-tetrazol-5-yl)-amide, 4-Oxo-4-{4-[2-(p-tolylsulphonamido)-ethyl]-phenyl}-butyric acid (1H-tetrazol-5-yl)-amide, 4-Hydroxy-4-{4-[2(4-chlorobenzenesulphonamido)-ethyl]-phenyl}-butyric acid (1H-tetrazol-5-yl)-amide, 5-{4-[2-(4-Chlorobenzenesulphonamido)-ethyl]-phenyl}-pentanoic acid (1H-tetrazol-5-yl)-amide, 3-[2-(4-bromobenzene-sulphonamido)-ethyl]-phenoxyacetic acid (1H-tetrazol-5-yl)-amide 5-{3-[2-(4-Chlorobenzenesulphonamido)-ethyl]-phenoxy-methyl}-1H-tetrazole.

* * * * *